(12) United States Patent
Chiu et al.

(10) Patent No.: US 7,442,170 B2
(45) Date of Patent: Oct. 28, 2008

(54) APPARATUS FOR PUNCH BIOPSY

(76) Inventors: Kwok Wai Chiu, 670 W. Arapaho Rd., Suite 6, Richardson, TX (US) 75080; Hongtao Qiu, 5936 E. Lovers La., Unit A207, Dallas, TX (US) 75206

( * ) Notice: Subject to any disclaimer, the term of this patent is extended or adjusted under 35 U.S.C. 154(b) by 94 days.

(21) Appl. No.: 11/426,313

(22) Filed: Jun. 25, 2006

(65) Prior Publication Data

US 2008/0039740 A1    Feb. 14, 2008

(51) Int. Cl.
*A61B 10/02*    (2006.01)
(52) U.S. Cl. ...................... 600/564; 606/167
(58) Field of Classification Search ............... 600/564; 606/167
See application file for complete search history.

(56) References Cited

U.S. PATENT DOCUMENTS

| | | | |
|---|---|---|---|
| 4,461,305 A * | 7/1984 | Cibley | 600/567 |
| 5,394,886 A * | 3/1995 | Nabai et al. | 600/567 |
| 5,827,199 A | 10/1998 | Alexander | |
| 2003/0212343 A1 * | 11/2003 | Plishka | 600/564 |
| 2006/0047219 A1 * | 3/2006 | Baruti et al. | 600/564 |

* cited by examiner

*Primary Examiner*—Max Hindenburg
*Assistant Examiner*—Renee Danega
(74) *Attorney, Agent, or Firm*—William S. Wang

(57) ABSTRACT

A punch biopsy apparatus for removing all or a portion of a suspect dermal growth. A punch biopsy apparatus has: a hollow cylinder body; a coring blade at the base of the hollow cylinder body; and a scooping blade assembly installed through a pair of installation channels and pivotally secured by a pair of pivot seats, where the scooping blade assembly comprises a semicircular scooping blade having actuating levers attached at each end via essentially rectangular connectors. This device helps minimize bleeding and minimize damage to the biopsy sample being retrieved.

6 Claims, 4 Drawing Sheets

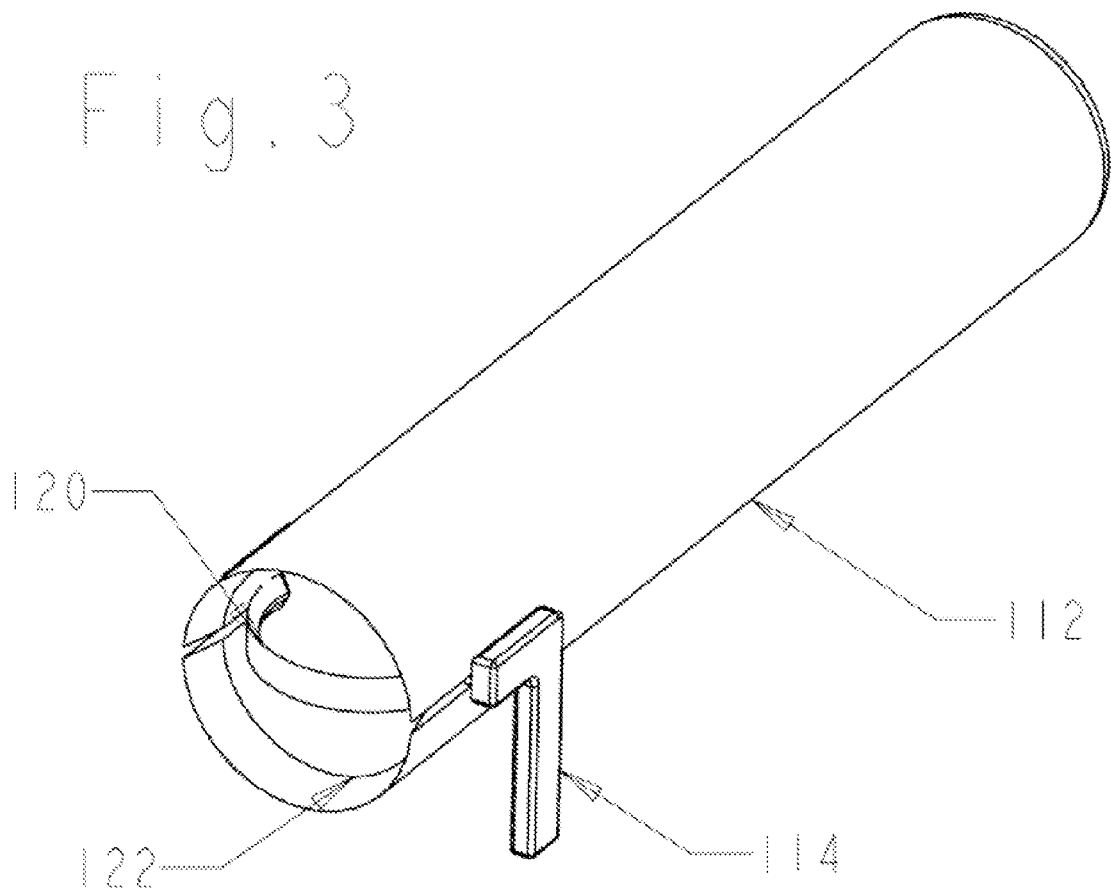

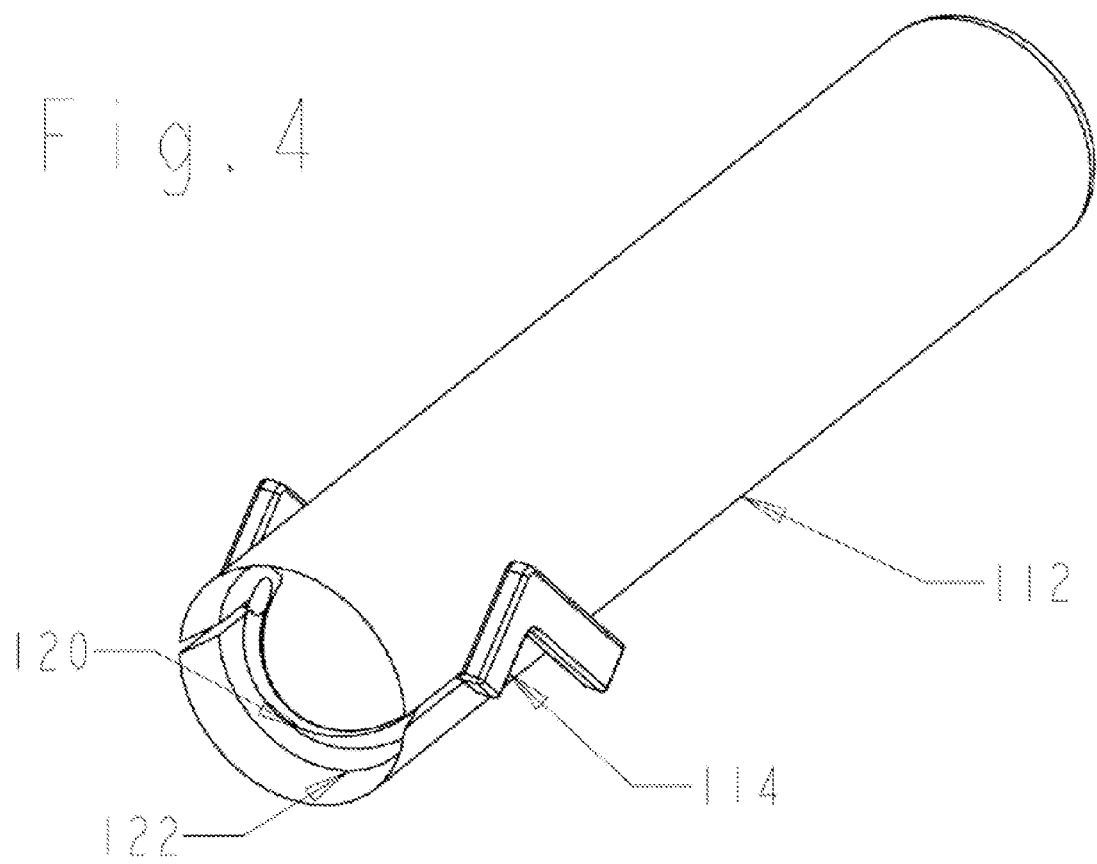

APPARATUS FOR PUNCH BIOPSY

BACKGROUND

1. Technical Field

The present invention relates to a punch biopsy apparatus for use in the surgical removal of all or part of a dermal (or skin) growth. More specifically, an improved punch biopsy apparatus enables biopsy removal with ease, efficiency, and minimal bleeding.

2. Description of Related Art

Skin biopsy is extremely useful in diagnosing potential dermatological disorders. In fact, many incorrect diagnoses occur due to a failure to perform a skin biopsy, or an improperly-executed biopsy. The most common technique used to obtain diagnostic, full-thickness dermatological samples is punch biopsy. The term "punch biopsy" refers to the nature of excising the suspect skin sample for analysis, which is akin to punching holes in a leather belt or punching holes in paper.

In the prior art, punch biopsy is typically performed using a circular blade or cylindrical blade. One specific example prior art device is a trephine, which is a surgical instrument having circular, saw-like edges, often used to cut out disks of bone, but which can also be used to remove cylindrical cores of skin. Such circular or cylindrical blade is rotated against and down through the epidermis first, then through the dermis, and finally into the subcutaneous lipid layer of the skin. When the practitioner is satisfied that the cylindrical blade has reached the appropriate depth, the practitioner then lifts the cored skin sample with either a pair of forceps or the anesthetic needle. While the skin sample is lifted, the sample is removed by cutting through the subcutaneous base with sharp tissue scissors or scalpel.

However, such rough handling of the sample can damage the sample to be tested. Crush artifact is particularly likely when forceps are used to raise the sample. Furthermore, the practitioner may not always be able to cut the base of the sample as low as desirable if the skin is too taught in the biopsy area.

Thus, a need exists for an improved surgical device for use in surgical procedures for removing skin biopsy samples. Such a device should be simple and easy to use even by doctors having minimal training and experience in surgical procedures.

SUMMARY OF THE INVENTION

According to the present invention, a punch biopsy apparatus has: a hollow cylinder body; a coring blade at the base of the hollow cylinder body; and a scooping blade assembly installed through a pair of installation channels and pivotally secured by a pair of pivot seats, where the scooping blade assembly comprises a semicircular scooping blade having actuating levers attached at each end via essentially rectangular connectors. This device helps minimize bleeding and minimize damage to the biopsy sample being retrieved.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 3 is a bottom perspective view of a preferred embodiment of a punch biopsy device with the scooping blade fully extended;

FIG. 4 is a bottom perspective view of a preferred embodiment of a punch biopsy device with the scooping blade and actuating lever canted at an appropriate angle for installing and/or removing the scooping blade.

REFERENCE NUMERALS

Figure 1:
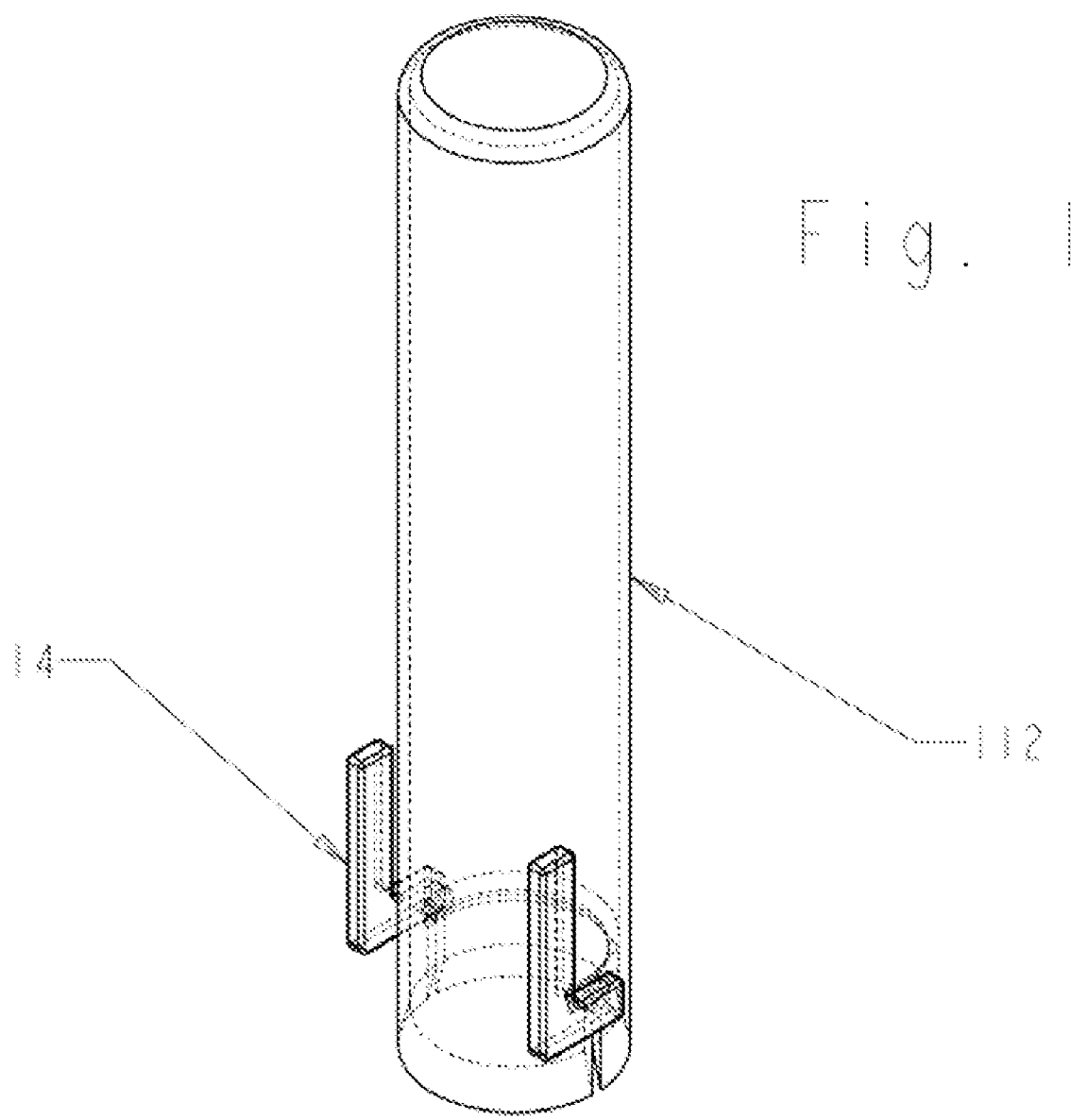
FIG. 1 is a side perspective view of a preferred embodiment of a punch biopsy device according to the present invention with the scooping blade fully retracted.
Figure 2:
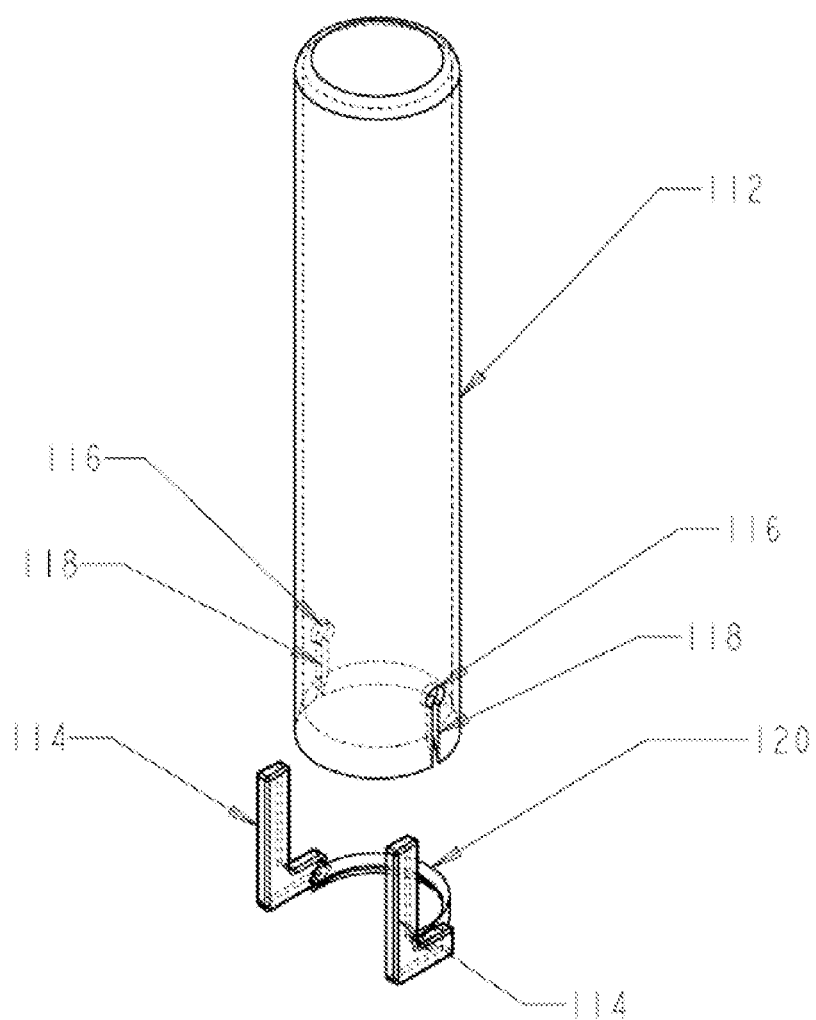
FIG. 2 is an enlarged perspective view of a preferred embodiment of a punch biopsy device with the scooping blade and actuating lever apart from the cylinder body.

112 cylinder body
114 actuating lever
116 pivot seat
118 installation channel
120 scooping blade
122 coring blade and coring-blade base

DETAILED DESCRIPTION

While the invention is described below with respect to a preferred embodiment, other embodiments are possible. The concepts disclosed herein apply equally to other instruments for retrieving core samples of other tissues, organs, organic matter, and can be applied to inorganic matter as well, provided that they follow the spirit of the teachings disclosed herein.

Whereas many prior art biopsy devices simply make vertical incisions but do not provide lateral incisions for detaching core samples, the present invention enables one to remove the desired portion of the skin by accomplishing both vertical and lateral incisions without employing a second instrument. Such contoured excision of the excess skin is made possible with the present punch biopsy device as disclosed herein.

According to the present invention, a punch biopsy apparatus has: a hollow cylinder body 112; a circular, beveled, coring blade 122 at the base of the hollow cylinder body 112; two circular pivot seats 116 near the base or the cylinder body 112; two longitudinal installation channels 118 at the base of the cylinder body 112 leading from the two circular pivot seats 116 down to the base of the cylinder body 112, essentially dividing the coring blade 122 into halves; and a scooping blade assembly installed through the installation channels 118 and pivotally secured by the pivot seats 116, where the scooping blade assembly comprises a semicircular scooping blade 120 having actuating levers 114 attached at each end via essentially oblong connectors (or pivot joints). This device helps minimize bleeding and minimize damage to the biopsy sample being retrieved. FIGS. 1-4 illustrate a preferred embodiment of this device.

The cylinder body 112 can be made of any sturdy, medical-grade material that can be sterilized and is suitable for containing tissue samples without cross-contamination and/or chemical leaching. Example materials include but are not limited to: stainless steel, biocompatible plastics, polymers, composites, ceramics, specialty and exotic metals, alloys, etc. In a preferred embodiment, stainless steel is used for all of the device components, including the cylinder body 112. The inner diameter of the cylinder body 112 is based upon the desired size of the biopsy to be taken. Thus, the inner diameter will typically range from about 2 millimeters (2 mm) to about 5 millimeters (5 mm). Preferably, the inner diameter will be between about 3 mm and about 4 mm. The thickness of the cylinder body 112 walls should be thick enough to withstand firm handling and twisting during biopsy procedures but should otherwise be as thin as possible.

The circular, beveled, coring blade 122 is located at the base of the cylinder body 112, and the thickness of the coring blade 122 tapers from its base or upper edge (where it meets the cylinder body 112) down to its sharp cutting edge or leading edge. The coring blade 122 is generally circular except for the pair of installation channels 118 essentially dividing the coring blade 122 into halves.

The scooping-blade assembly comprises a scooping blade 120 and a pair of actuating levers 114 at either end of the scooping blade 120. Each arm of the pair of actuating levers 114 is preferably L-shaped, but other shapes are also suitable. The actuating levers 114 are connected to the scooping blade 120 at each side by rectangular or otherwise oblong joints having a thickness of at least that of the walls of the cylinder body 112. These rectangular or oblong pivot joints should be such that the scooping-blade assembly slides into the complementary installation channels 118 in a specific orientation but not at any other angle. For example, the rectangular joints depicted in FIGS. 1-4 prevent the scooping assembly from accidentally detaching from the bottom of the cylinder body. The rectangular joints are small enough to completely fit within their corresponding pivot seats, yet large enough so that they must be aligned precisely lengthwise (relative to the installation channels 118) to pass through the installation channels 118. Such an arrangement allows the practitioner to pivot the scooping-blade assembly about the pivot joints during operation without fear of accidental detachment, so long as the practitioner does not simultaneously lift the cylinder body 112 while the pivot joints are precisely aligned lengthwise with the installation channels 118. Because the scooping blade 120 only needs to rotate approximately 90 degrees during operation, the long axes of the pivot joints are preferably oriented at such an angle so that the long axes will never align with the installation channels 118 during normal use. Thus, the pivot joints (or oblong connectors) point at an angle between the actuating lever arms 114 and the scooping blade 120. In a preferred embodiment, the long axes of the pivot joints are oriented about 45 degrees from the scooping blade's 120 plane of curvature.

The scooping blade 120 should be beveled (or otherwise thicker along the center for strength) and sharp on both edges so that the scooping blade 120, when fully extended (i.e. the axis of curvature of the scooping blade is perpendicular to the cylinder body's axis), can carve through the dermis and lipid layers to be sampled. The diameter of the scooping blade 120 should be slightly less than the inner diameter of the cylinder body 112 such that the scooping blade 120 can pivot freely about its pivot joints when seated within the pivot seats and enclosed within the cylinder body 112.

In practice, the selected area of the skin is cleaned with a sterilizing solution such as povidone-iodine solution and anesthetized using, for example, a lidocaine-with-epinephrine solution. The sterilized biopsy device of the present invention is assembled by aligning the pivot joints with the installation channels 118 and sliding the scooping-blade assembly up into the cylinder body 112 until the pivot joints reach the pivot seats 116. The scooping-blade assembly is then rotated slightly about its pivot joints held within the pivot seats 116 until the scooping blade 120 is flush with the inner surface of the cylinder body 112. Next, the entire biopsy device is held vertically over the portion of the skin to be sampled, and the device is simultaneously rotated and pushed downward to cause the biopsy device's coring blade 122 to penetrate the skin. Once the practitioner reaches the desired depth (typically breaking through the dermis and into the subcutaneous lipid layers), the actuating lever arms 114 are used to rotate the scooping blade 120 from a fully-retracted position (as shown in FIG. 1) to a fully-extended position (as shown in FIG. 3). This 90-degree rotation causes the scooping blade 120 to make a semi-spherical incision at the bottom of the cylinder body 112. Once fully extended, the scooping blade 120 is spun about the center axis of the cylinder body 112. This spinning of the cylinder body 112 and scooping blade 120 causes the scooping blade 120 to sculpt a hemispherical bottom for the cored skin sample, thereby detaching the biopsy sample from the lower layers prior to lifting and/or removing the sample. In the event that a simple, single 90-degree motion of the scooping blade 120 is too difficult to perform (which may happen due to the toughness of the sampling area, etc.), such rotation of the scooping blade 120 can be performed simultaneously with a continued spinning motion of the cylinder body 112, thereby easing the coring and detaching steps. Once the tissue has been cored and detached from the lower layers (by scooping the sample bottom), the entire biopsy device and the biopsy specimen can be lifted vertically and without further incision. In its fully-extended position, the scooping blade 120 also serves as a retaining cross-member for retaining the biopsy specimen within the cylinder body 112 during lifting and removal, of the biopsy device. The actuating lever arms 114 can be returned to their starting positions to retract the scooping blade 120 and release the biopsy specimen.

While the invention has been particularly shown and described with reference to a preferred embodiment, it will be understood by those skilled in the art that various changes in form and detail may be made therein without departing from the spirit and scope of the invention.

We claim:

1. A biopsy device for assisting in the removal of a biopsy specimen, said biopsy clamp comprising:
   a hollow cylinder body;
   a circular, beveled, coring blade at the base of the hollow cylinder body;
   two circular pivot seats located on the cylinder body, near the base of the cylinder body;
   two longitudinal installation channels, also located on the cylinder body and near the base of the cylinder body, leading from the two circular pivot seats, cutting through the cylinder body, down to the base of the cylinder body, thereby dividing the coring blade into halves; and
   a scooping blade assembly installed through the installation channels and pivotally secured by the pivot seats, where the scooping blade assembly comprises a semi-circular scooping blade having two actuating lever arms, one attached at each end of the scooping blade via essentially oblong connectors.

2. The biopsy device of claim 1 wherein said biopsy device is made of a medical-grade stainless steel.

3. The biopsy device of claim 1 wherein the inner diameter of the cylinder body is within the range of about 2 mm to about 5 mm.

4. The biopsy device of claim 1 wherein the inner diameter of the cylinder body is within the range of about 3 mm to about 4 mm.

5. The biopsy device of claim 1 wherein the oblong connectors are rectangular.

6. The biopsy device of claim 1 wherein the oblong connectors are oriented at an angle between the actuating lever arms and the scooping blade.

* * * * *